(12) United States Patent
Vogtmeier et al.

(10) Patent No.: US 10,912,527 B2
(45) Date of Patent: Feb. 9, 2021

(54) APPARATUS FOR GENERATING DUAL ENERGY IMAGING DATA

(71) Applicant: KONINKLIJKE PHILIPS N.V., Eindhoven (NL)

(72) Inventors: Gereon Vogtmeier, Aachen (DE); Roger Steadman Booker, Aachen (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 16/772,530

(22) PCT Filed: Dec. 27, 2018

(86) PCT No.: PCT/EP2018/086891
§ 371 (c)(1),
(2) Date: Jun. 12, 2020

(87) PCT Pub. No.: WO2019/134881
PCT Pub. Date: Jul. 11, 2019

(65) Prior Publication Data
US 2020/0375556 A1    Dec. 3, 2020

(30) Foreign Application Priority Data
Jan. 5, 2018 (EP) ..................................... 18150427

(51) Int. Cl.
*A61B 6/00* (2006.01)
*A61B 6/03* (2006.01)

(52) U.S. Cl.
CPC ............ *A61B 6/4035* (2013.01); *A61B 6/032* (2013.01); *A61B 6/4021* (2013.01); *A61B 6/482* (2013.01); *A61B 6/54* (2013.01)

(58) Field of Classification Search
CPC ......... A61B 6/4035; A61B 6/54; A61B 6/482; A61B 6/4021; A61B 6/032
(Continued)

(56) References Cited

U.S. PATENT DOCUMENTS

| 4,145,616 A | 3/1979 | Tanabe |
| 5,949,811 A * | 9/1999 | Baba .................... A61B 6/4225 378/108 |

(Continued)

FOREIGN PATENT DOCUMENTS

| JP | 2002027082 A | 1/2002 |
| JP | 2009082173 A | 4/2009 |

(Continued)

OTHER PUBLICATIONS

PCT International Search Report, International application No. PCT/EP2018/086891, dated Mar. 21, 2019.
(Continued)

*Primary Examiner* — David P Porta
*Assistant Examiner* — Gisselle M Gutierrez
(74) *Attorney, Agent, or Firm* — Larry Liberchuk

(57) ABSTRACT

The present invention relates to an apparatus for generating dual energy X-ray imaging data. It is described to position (210) an X-ray detector relative to an X-ray source such that at least a part of a region between the X-ray source and the X-ray detector is an examination region for accommodating an object. A grid filter is positioned (220) between the examination region and the X-ray source. The X-ray source produces (230) a focal spot on a target to produce X-rays. The X-ray source moves (240) the focal spot in a first direction across a surface of the target. The grid filter has a structure in a first orientation such that the movement of the focal spot in the first direction results in an associated change in an intensity of X-rays transmitted by the grid filter. The X-ray source moves (250) the focal spot in a second direction across the surface of the target that is orthogonal to the first direction. The grid filter has a structure in a second orientation orthogonal to the first orientation such that the movement of the focal spot in the second direction results in
(Continued)

an associated change in an energy spectrum of X-rays transmitted by the grid filter. The X-ray detector detects (260) at least some of the X-rays transmitted by the grid filter.

13 Claims, 3 Drawing Sheets

(58) Field of Classification Search
USPC .................................................................. 378/5
See application file for complete search history.

(56) References Cited

U.S. PATENT DOCUMENTS

| | | |
|---|---|---|
| 9,295,437 B2 | 3/2016 | Saito |
| 9,424,958 B2 | 8/2016 | Vogtmeier |
| 2006/0023832 A1 | 2/2006 | Edic |
| 2012/0020454 A1 | 1/2012 | Murakoshi |
| 2012/0099709 A1 | 4/2012 | Thesen |
| 2013/0266115 A1 | 10/2013 | Fan |
| 2014/0112441 A1 | 4/2014 | Becker |
| 2014/0177807 A1 | 6/2014 | Lewellen |
| 2016/0113602 A1 | 4/2016 | Wang |
| 2016/0338653 A1 | 11/2016 | Behling |
| 2017/0011815 A1 | 1/2017 | Pack |
| 2017/0053772 A1 | 2/2017 | Mackie |

FOREIGN PATENT DOCUMENTS

| | | |
|---|---|---|
| JP | 2013195407 A | 9/2013 |
| WO | WO2017133366 A1 | 10/2017 |
| WO | WO2017176976 A1 | 10/2017 |

OTHER PUBLICATIONS

Fenglin Liu et al., "Dynamic Bowtie Filter for Cone-Beam/Multi-Slice CT", PL0S ONE, vol. 9, No. 7, Jul. 22, 2014.

* cited by examiner

APPARATUS FOR GENERATING DUAL ENERGY IMAGING DATA

FIELD OF THE INVENTION

The present invention relates to an apparatus for generating dual energy imaging data, to a system for generating dual energy imaging data, to a method for generating dual energy imaging data, as well as to a computer program element and a computer readable medium.

BACKGROUND OF THE INVENTION

The general background of this invention is the field of X-ray spectral computed tomography (CT). In a CT system an X-ray source emits X-ray radiation. The emitted radiation traverses an examination region with a subject or object located within and is detected by a detector array opposite the X-ray source. The detector array detects the radiation traversing the examination region and the subject and generates projection data, e.g. raw detector data or projection images. A reconstructor processes the projection data and reconstructs a volumetric image of the subject or object. X-ray Spectral CT is an imaging modality that extends the capabilities of a conventional CT system. Dual-Energy (DE) CT, which is a specific configuration of spectral CT, utilizes two attenuation values acquired at two distinct energy spectra to solve the photoelectric and Compton contribution that consists of the mass attenuation coefficient of a material, and thus to identify an unknown material by its value of photoelectric and Compton contribution. This scheme works especially well in materials such as iodine because Iodine can be differentiated from for example calcium due to photo-electric/Compton properties. Because any two linearly independent sums of two basis functions span the entire attenuation coefficient space, any material can be represented by a linear combination of two other materials, so called basis materials, such as water and iodine. The basis material images provide new applications such as monochromatic image, material cancellation image, effective atomic number image and electron density image. There are several approaches to perform dual energy CT acquisition such as dual-source, fast kVp switching, and dual-layer detector configurations. However, such approaches can be expensive. At the same time, the object being examined, such as the body of a patient is not rotationally symmetrical. For instance, normally patients are somewhat elliptical in their cross-section, with the front-rear direction normally being thinner than the left-right direction. A dose saving can be achieved by reducing the X-ray flux (equivalent to X-ray intensity for an acquisition having a set period of time) when the gantry is positioned in the front-rear (or rear-front) direction. However, dose modulation is not easy on the fast timescale of gantry rotation (several Hz). Changing the current is normally too slow due to the high capacity of the high voltage cables and the need to thermally control the cathode. Grid switching is a fast way to control the beam current in an X-ray tube by electrostatically pinching the beam. Ideally, one can switch from full current to zero current in a few microseconds. This makes pulse width modulation (PWM) of the X-ray intensity possible by changing the duty cycle of the electron beam. PWM is a flexible way to achieve intensity modulation in a fast way. It however requires expensive generator electronics and not all X-ray tubes in the field are equipped with these, and to facilitate dual energy acquisition at the same time can make systems prohibitively expensive.

There is a need to address these issues.

SUMMARY OF THE INVENTION

It would be advantageous to have an improved apparatus for generating dual energy imaging data.

The object of the present invention is solved with the subject matter of the independent claims, wherein further embodiments are incorporated in the dependent claims. It should be noted that the following described aspects and examples of the invention apply also to the apparatus for generating dual energy imaging data, the system for generating dual energy imaging data, the method for generating dual energy imaging data and for the computer program element and the computer readable medium.

According to a first aspect, there is provided an apparatus for generating dual energy X-ray imaging data, comprising:

an X-ray source;
a grid filter; and
an X-ray detector.

The X-ray source is configured to produce a focal spot on a target to produce X-rays. The X-ray source is configured also to move the focal spot in a first direction across a surface of the target. The X-ray source is configured also to move the focal spot in a second direction across the surface of the target that is orthogonal to the first direction. The X-ray detector is positioned relative to the X-ray source such that at least a part of a region between the X-ray source and the X-ray detector is an examination region for accommodating an object. The grid filter is positioned between the examination region and the X-ray source. The grid filter has a structure in a first orientation such that a movement of the focal spot in the first direction is configured to result in an associated change in an intensity of X-rays transmitted by the grid filter. The grid filter has a structure in a second orientation orthogonal to the first orientation such that a movement of the focal spot in the second direction is configured to result in an associated change in an energy spectrum of X-rays transmitted by the grid filter. The X-ray detector is configured to detect at least some of the X-rays transmitted by the grid filter.

In other words, a grid filter is used that provides for intensity modulation and in this way as the X-ray source and detector rotate about an object, such as a human body that does not have a constant cross section as a function of rotational position, the intensity of X-rays can be modulated to match the depth through the target to optimize dosage. This is done by the focal spot from which X-rays are emitting from a target moving (or being moved in that the electron beam focal spot need not be on when being moved from one position to another) in a first direction, such that the x-rays are now emitted from a different position from the X-ray source and then have slightly different paths through a grid filter, with the change in path leading to a change in overall intensity due to the structure of the grid filter in the associated direction of movement. At the same time (same time here referring to example as a gantry rotates and does not necessarily mean exactly at the same time) by moving the point of emission of X-rays in the orthogonal direction, the grid filter is structured such that the different routes of X-rays through the filter interact with different materials and in this way the spectrum of the X-rays can be changed, for example from a first energy spectrum to a second energy spectrum. Thus in this way, a dual energy apparatus is provided that can modulate the energy spectrum extremely rapidly as an x-ray source and X-ray detector rotate about a target through the focal spot being focused at two points spaced apart in one direction, and at the same time a less rapid movement of the focal spot in the orthogonal direction can modulate the intensity of the X-ray beam in order to optimize dosage levels as the thickness through the object changes.

In this manner, for each intensity level obtained by positioning the focal spot at a first "position" through movement in the first direction to obtain this intensity level the focal spot at that "position" can be moved in the second direction to modulate the X-rays from one energy spectrum to a different energy spectrum, thus providing the dual energy capability with variable intensity capability.

To put this another way, modulation is provided via a change in the passage of X-rays through a grid filter effected by a movement of the emission point of X-rays from the X-ray source in a first direction that enables the beam intensity profile to be adapted to the inverse of the patient body depending on the angular gantry position. This allows for optimal intensity profiles. At the same time a spectral modulation is provided via a change in the passage of X-rays through the grid filter effected by a movement of the emission point of X-rays from the X-ray source in a second direction orthogonal to the first direction, thus such position changes can be achieved from frame to frame (or from multiple frames to multiple frames, or asymmetrically with one frame at a given spectrum and N frames at a second given spectrum, e.g.: 1:2; 1:3, 1:5 . . . ) enabling a dual energy data set to be provided at all angular positions, where fast switching of the focal spot in the second direction enables the two different energy spectra of the patient to be acquired at virtually the same gantry angular position.

Control of the emission point of the X-rays from the X-ray source in two orthogonal directions providing for associated changes in X-ray beam directions through the grid filter to provide for both intensity and energy spectrum modulation enables great flexibility in the acquisition protocols and also allows image acquisitions that are compatible with most of the old CT systems (in other words, the present apparatus features can be retro-fitted to existing CT systems) providing for an efficient and cost effective way to achieve dual energy acquisitions at the required dosage levels.

In an example, the grid filter has a focal length associated with the structure in the first orientation, and wherein the grid filter is spaced away from the focal spot of the X-ray source by a distance equal to the focal length.

In this way, at one position of the focal spot the grid filter has a maximum in intensity and movements in the first direction leads to an overall reduction in intensity across the extent of the X-ray beam and for all energies. Any energy dependence effects are much less than those for the spectral grid, however from knowledge of the material properties for the grid filter used energy dependence effects can be calculated and be taken into account. Rather than calculations, a calibration of spectra with movement can be undertaken.

In other words a filter made up from a grating or focused grid-like structure close to X-ray tube can also be used to modulate the X-ray flux exiting this filter by using deflection of the focal spot in a first direction. The deflection can be used to modulate the X-ray flux in a fast and dynamic way together with a grating or grid-like structure close to the tube. In this way it is enables to change the X-ray flux of the tube by placing the grid-like structure very close to the X-ray tube (so on the other side of the patient compared to normal anti-scatter grid use). By using a focused grid with a focal distance equal to the distance to the X-ray focus it is assured that the transmission of X-rays through the grid yields a flat profile for all shifts of the focal spot. However only for one (nominal) position the transmission is maximal and shifting the focal spot away from this position yields a lower overall transmission. In this way it is able to modulate the flux in a very fast way without having any mechanically moving parts, providing for a fast changing intensity that matches the changing cross section of a patient viewed as the gantry rotates.

In an example, the structure in the first orientation comprises a plurality of first lamellae spaced apart from one another. The first lamellae are made of a first material and wherein the grid filter between the first lamellae is made of the first material or a material relatively transparent to X-rays.

In this way, movement of the focal spot in the first direction leads to X-rays passing through different thicknesses of the first material and thus the overall intensity is modulated and the energy spectrum stays the same as there has only been a change in the amount of material through which x-rays must pass. As discussed above, any change in spectra can be accounted for via calculations or a calibration.

In an example, the plurality of first lamellae point towards a line on the target such that the focal spot when focused at a position on that line is associated with maximum X-ray transmission with respect to movement in the first direction.

In other words, a 1-dimensional grating or filter structure is provided with lamellae extending away from a grating plane that point towards a focal line on the target. When the focal spot is focused on that line a local maximum is intensity is obtained because the X-rays interacting with the grating or grid filter propagate through the grid filter parallel to the lamellae with most of the X-rays interacting with the thinner material between the lamellae (or a transparent material between the lamellae) with a fraction of the X-rays interacting with the lamellae. However, a movement of the focal spot in the first direction leads to the X-rays now angling through the grid filter such that the X-rays are not now parallel to the lamellae and thus the movement in the first direction leads to an associated known change in the intensity of the X-rays. In this manner intensity modulation is provided for an invariant energy spectrum. As discussed above, a certain amount of hardening can occur, but this is correctable.

In an example, the structure in the first orientation comprises a spatially varying absorbing profile with a minimum absorption associated with the center of the plurality of first lamellae and an increasing absorption profile associated with the structure in the first orientation extending either side of the center of the first lamellae.

In other words, the 1-D grating associated with the structure in the first orientation has an underlying Bowtie absorption profile, providing for a maximum intensity of X-rays at a center plane with decreasing X-ray intensities with movement away from the center plane that can account for an object such as a human body for a fixed viewing angle having a maximum thickness at the center that becomes thinner towards the edges of the body. However, because the body is not cylindrical with a circular cross-section, but rather has an elliptical type cross section, as the viewing orientation changes the centerline thickness changes, and the movement of the focal spot leads to a change in the overall intensity of the inverse Bowtie intensity to maintain the required dosage. Thus in one orientation, the grid filter acts as a dynamic Bowtie filter enabling a change in intensity of the Bowtie with a movement of the focal spot in the first direction. Whilst at the same time, dual energy capability is provided through movement of the focal spot in the second orthogonal direction.

In an example, the spatially varying absorption profile comprises a variation in the thickness of individual ones of the plurality of first lamellae.

In an example, the structure in the first orientation comprises a plurality of further lamellae spaced apart from one another and spaced laterally from the plurality first lamellae. The structure in the first orientation comprises a spatially varying absorbing profile with a minimum absorption associated with the center of the plurality of further lamellae. An increasing absorption profile associated with the structure in the first orientation extends either side of the center of the further lamellae that is different to the increasing absorption profile associated with the structure in the first orientation extending either side of the center of the first lamellae.

In an example, the plurality of further lamellae point towards a line on the target such that the focal spot when focused at a position on that line is associated with maximum X-ray transmission with respect to movement in the first direction.

In other words, in the first orientation the grid filter does not have just one dynamic bowtie associated with one set of lamellae, but has a second dynamic bowtie associated with another set of lamella to the side of the first set of lamellae. In this way, movements of the focal spot in the first direction can lead to a change of intensity of a bowtie associated with one set of lamellae. Then, a much larger movement of focal spot in the first direction can lead to X-rays interacting with a different set of lamellae of the grid filter to provide a second dynamic Bowtie. For example, one Bowtie could be commensurate with interaction with small objects such as the bodies of children providing for the required dosage levels across the body, whilst a second bowtie could be commensurate with interactions with adult bodies. There can additionally be third or fourth bowties provided in this manner.

In an example, the grid filter has a focal length associated with the structure in the second orientation. The grid filter is spaced away from the focal spot of the X-ray source by a distance equal to the focal length.

In this way, at one position of the focal spot the grid filter has a maximum in intensity.

In an example, the structure in the second orientation comprises a plurality of second lamellae spaced apart from one another. The second lamellae are made of a different material to the first lamella.

In an example, the structure in the second orientation comprises a plurality of sections with different materials for different basic filtration.

In this way, when at a maximum intensity the X-rays emitted by the source only propagate through the first material a certain fraction of the different material of the second lamellae and have a first energy spectrum. However, movement of the focal spot in the second direction leads to X-rays now propagating also more of the second material, that of the second lamellae, and as such the energy spectrum is changes. In other words, movement of the electron beam focal spot in the second direction from a first position to a second position has enabled a first x-ray beam to be provided with a first energy spectrum associated with the first position and then enables a second X-ray beam to be provided with a second energy spectrum associated with the second position. Thus, dual energy X-rays beams can be efficiently provided, and at the same time movement of the emission point of the X-rays in the first direction enables the intensity of the x-rays to be changed without changing the energy spectrum.

Thus, the second lamellae are orthogonal to the first lamellae. In an example, the second lamellae are stacked on top of the first lamellae. In an example, the first lamella are stacked on top of the second lamellae. In an example, the first and second lamellae are positioned substantially in the same plane, forming a criss-cross pattern in that plane, such that certain ones of the lamellae of the first lamellae extend through certain ones of the lamellae of the second lamellae and vice versa.

In an example, the plurality of second lamellae point towards the focal spot when at the position associated with maximum X-ray transmission.

In other words, the grid filter has a second a 1-dimensional grating or filter structure is provided with lamellae extending away from a grating plane that point towards a focal line on the target, with this focal line on the target orthogonal to the focal line associated with the plurality of first lamellae. When the focal spot is focused on that line a local maximum is intensity is obtained because the X-rays interacting with the grating or grid filter propagate through the grid filter parallel to the lamellae with most of the X-rays interacting with the thinner material between the lamellae with a fraction of the X-rays interacting with the lamellae. Thus X-rays will have a characteristic spectrum associated with transmission through the first lamellae and the material between the lamellae that is the same as the first lamellae and associated with transmission through a small amount of the material of the second lamellae. However, a movement of the focal spot in the second direction leads to the X-rays now angling through the grid filter such that the X-rays are not now parallel to the plurality of second lamellae but there is no change to interaction with the first lamellae, and as such the X-ray spectrum of x-rays passing through the grid filter is now characterized by that associated with increased transmission through the material of the second lamellae. Thus movement of the focal spot in the second direction, enables the X-rays transmitted by the grid filter to be modulated between two different and known energy spectrums, providing for dual energy capabilities with intensity modulation to account for non-circularly symmetric target geometries.

According to a second aspect, there is provided a system for X-ray imaging an object, comprising:

an apparatus for generating dual energy X-ray imaging data according to the first aspect;

a processing unit; and an output unit,

The processing unit is configured to control the apparatus, and is configured to control the output unit. The X-ray detector is configured to provide the processing unit with data relating to the detection of X-rays. The output unit is configured to output data representative of the object.

According to a third aspect, there is provided a method for generating dual energy X-ray imaging data, comprising:

a) positioning an X-ray detector relative to an X-ray source such that at least a part of a region between the X-ray source and the X-ray detector is an examination region for accommodating an object;

b) positioning a grid filter between the examination region and the X-ray source;

c) producing by the X-ray source a focal spot on a target to produce X-rays;

d) moving by the X-ray source the focal spot in a first direction across a surface of the target; wherein, the grid filter has a structure in a first orientation such that the movement of the focal spot in the first direction results in an associated change in an intensity of X-rays transmitted by the grid filter;

e) moving by the X-ray source the focal spot in a second direction across the surface of the target that is orthogonal to the first direction; wherein, the grid filter has a structure in a second orientation orthogonal to the first orientation such that the movement of the focal spot in the second direction results in an associated change in an energy spectrum of X-rays transmitted by the grid filter;

f) detecting with the X-ray detector at least some of the X-rays transmitted by the grid filter.

According to another aspect, there is provided a computer program element controlling apparatus as previously described which, when the computer program element is executed by a processing unit, is adapted to perform the method steps as previously described.

According to another aspect, there is provided a computer readable medium having stored computer element as previously described.

Advantageously, the benefits provided by any of the above aspects equally apply to all of the other aspects and vice versa.

The above aspects and examples will become apparent from and be elucidated with reference to the embodiments described hereinafter.

BRIEF DESCRIPTION OF THE DRAWINGS

Exemplary embodiments will be described in the following with reference to the following drawings.

DETAILED DESCRIPTION OF EMBODIMENTS

Figure 1:
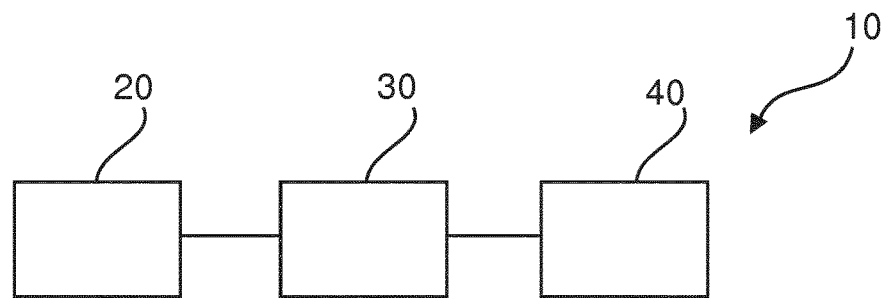
FIG. 1 shows a schematic set up of an example of an apparatus for generating dual energy imaging data.

FIG. 1 shows an example of an apparatus 10 for generating dual energy X-ray imaging data. The apparatus 10 comprises an X-ray source 20, a grid filter 30, and an X-ray detector 40. The X-ray source 20 is configured to produce a focal spot on a target to produce X-rays. The X-ray source 20 is configured also to move the focal spot in a first direction across a surface of the target. The X-ray source 20 is configured also to move the focal spot in a second direction across the surface of the target that is orthogonal to the first direction. The X-ray detector 40 is positioned relative to the X-ray source 20 such that at least a part of a region between the X-ray source 20 and the X-ray detector 40 is an examination region for accommodating an object. The grid filter 30 is positioned between the examination region and the X-ray source 20. The grid filter 30 has a structure in a first orientation such that a movement of the focal spot in the first direction is configured to result in an associated change in an intensity of X-rays transmitted by the grid filter 30. The grid filter 30 also has a structure in a second orientation orthogonal to the first orientation such that a movement of the focal spot in the second direction is configured to result in an associated change in an energy spectrum of X-rays transmitted by the grid filter 30. The X-ray detector 40 is configured to detect at least some of the X-rays transmitted by the grid filter.

In an example, the material of the structure in the first orientation of the grid filter can be any one or more of: Molybdenum, Tungsten, Lead, Aluminium, and the material of the structure in the second orientation of the grid filter can be any one or more of: Molybdenum, Tungsten, Lead, Aluminium, Titanium, Tin (and more) but being a different material or material combination to the material of the structure in the first orientation such that a movement in the second direction leads to a change in x-ray energy spectrum.

In an example a frequency of movement in the second direction is greater than a frequency of movement in the first direction. In an example, a frequency of in the second direction is more than an order of magnitude greater than a frequency of movement in the first direction. Thus, intensity modulation of achieved through movement of in the first direction can be via relatively low frequency movements that gradually changes the intensity of the X-ray beam to match the changing thickness of the object being viewed. However, very fine adjustments in the first direction could be made to provide a semi-continuous change in intensity. There is therefore a link between the fidelity of movement and the frequency of modulation, with fine adjustments being made more frequently than larger movements. At the same time, movement in the second direction, rather than being movements that lead to gradual changes, can be step movements from a first position to a second position, and then back to a first position again in order to provide X-ray beams with two different energy spectra. The switching back and forth can be then at a very high frequency, such that a gantry rotating about an object has not moved substantially for the two different X-ray beams, providing for dual beam imaging from which material features of the object and/or Compton Scattering and Photoelectric scattering coefficients can be determined in order to provide an extra degree of information from the X-ray apparatus. Indeed, in the second direction the movement could be from a first to a second and to a third position, with movement back to the first position and repeated or other combinations of movements being effected. However, at each position the X-ray beam will have a different energy spectrum, and therefore in addition to dual energy imaging, tri-energy or even quad-energy imaging is possible, enabling an increased number of materials to be separated one from the other following appropriate processing.

According to an example, the grid filter has a focal length associated with the structure in the first orientation. The grid filter is then spaced away from the focal spot of the X-ray source by a distance equal to the focal length.

According to an example, the structure in the first orientation comprises a plurality of first lamellae spaced apart from one another. The first lamellae are made of a first material and the grid filter between the first lamellae is made of the first material or a material relatively transparent to X-rays.

In an example, by placing the grid filter not close to the detector but close to the X-ray source and also having the grid filter in the first orientation a very short focal distance equal to its distance to the X-ray source, it is able to exploit a phenomenon of homogenous transmission changes with focal spot movement in the first direction to modulate the X-ray flux passing the grid by electronically steering the electron beam away from its ideal nominal position in the first direction. Only small deviations in the order of millimeters have to be accomplished to obtain relatively large decreases in transmission. An analytical formula which can be used to calculate the transmission for arbitrary shifts in the first direction.

$$Tp^{shift} = Tp^{ideal}\left(1 - \frac{r|X|}{f}\right)$$

Where r is the ratio of the grid (i.e. the aspect ratio of the interspacer material) and f is the nominal focal distance of the grid. For a modest grid ratio of 10 and a focal distance of 100 mm, a 1 mm shift would give a decrease of transmission of 10%.

According to an example, the plurality of first lamellae point towards a line on the target such that the focal spot when focused at a position on that line is associated with maximum X-ray transmission with respect to movement in the first direction.

According to an example, the structure in the first orientation comprises a spatially varying absorbing profile with a minimum absorption associated with the center of the plurality of first lamellae. The grid filter also has an increasing absorption profile associated with the structure in the first orientation extending either side of the center of the first lamellae.

In an example, the spatially varying absorption profile comprises a variation in the thickness of the material between the plurality of first lamellae. In other words, the grid filter can be thinner at the center of the plurality of first lamellae and become thicker with movement away from the center of the plurality of first lamellae.

According to an example, the spatially varying absorption profile comprises a variation in the thickness of individual ones of the plurality of first lamellae.

In an example, the spatially varying absorption profile comprises a variation in the tilt angle of individual ones of the plurality of first lamellae.

According to an example, the structure in the first orientation comprises a plurality of further lamellae spaced apart from one another and spaced laterally from the plurality first lamellae. The structure in the first orientation then comprises a spatially varying absorbing profile with a minimum absorption associated with the center of the plurality of further lamellae. The grid filter also has an increasing absorption profile associated with the structure in the first orientation extending either side of the center of the further lamellae that is different to the increasing absorption profile associated with the structure in the first orientation extending either side of the center of the first lamellae.

In an example, the further lamellae are made of the first material and the material between the further lamellae are made of the first material or the material relatively transparent to X-rays.

In an example, with respect to a larger "jump" of the focal spot to different subsections of the lamellas (still intensity grid) to interact with different Bow Tie structures, some position compensation can be necessary to move the ASG in total with respect to the sub-segments. In this way, adjustment of the ASG to the focal spot enables symmetrical performance to be provided.

According to an example, the plurality of further lamellae point towards a line on the target such that the focal spot when focused at a position on that line is associated with maximum X-ray transmission with respect to movement in the first direction.

In an example, the plurality of further lamellae are made of the same material as the first lamellae, and it is through the thicknesses and tilting angles of individual lamellae of the further lamellae are used to provide the required Bowtie absorption profile.

According to an example, the grid filter has a focal length associated with the structure in the second orientation. The grid filter is then spaced away from the focal spot of the X-ray source by a distance equal to the focal length.

According to an example, the structure in the second orientation comprises a plurality of second lamellae spaced apart from one another. The second lamellae are made of a different material to the first lamella.

According to an example, the plurality of second lamellae point towards the focal spot when at the position associated with maximum X-ray transmission.

Figure 2:
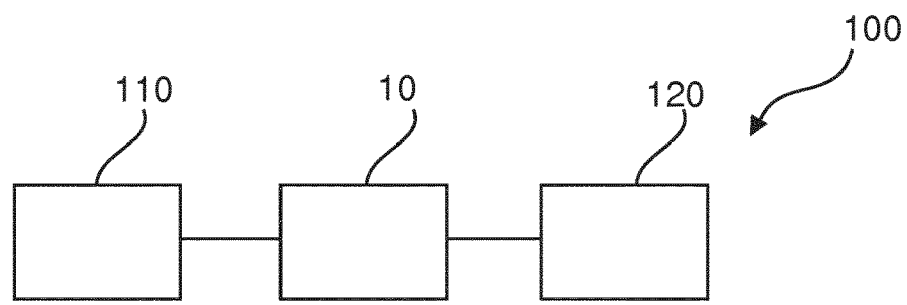
FIG. 2 shows a schematic set up of an example of a system for generating dual energy imaging data.

FIG. 2 shows an example of a system 100 for X-ray imaging an object. The system 100 comprises an apparatus 10 for generating dual energy X-ray imaging data as described above with respect to FIG. 1. The system 100 also comprises a processing unit 110, and an output unit 120. The processing unit 110 is configured to control the apparatus 10, and is configured to control the output unit 120. The X-ray detector 40 is configured to provide the processing unit with data relating to the detection of X-rays. The output unit 120 is configured to output data representative of the object.

In an example, the output unit is configured to output data representative of the X-ray transmission of the at least part of the object.

In an example, the output unit is configured to output data dual energy data. Thus, for example the system enables two basis sets of multi energy data for an object to be generated from the dual energy data. The two basis sets could be data such as Compton data and Photoelectric data, or data sets for two materials such as water and iodine. The basis sets, Compton, Photoelectric, Water, Iodine, can be considered to be "base materials" and do not need to relate to real materials, but can also be considered to be virtual materials. However, the region of interest of the object can then be represented in the multi energy domain, for example being represented as two images one of water and one or iodine, or one of Compton scatter and one of Photoelectric scatter etc. In this manner the present system enables dual energy data, from which further information in addition to attenuation data, can be derived and does this in a simple manner that can be combined with an x-ray beam the intensity of which is modified to match the object size.

Figure 3:
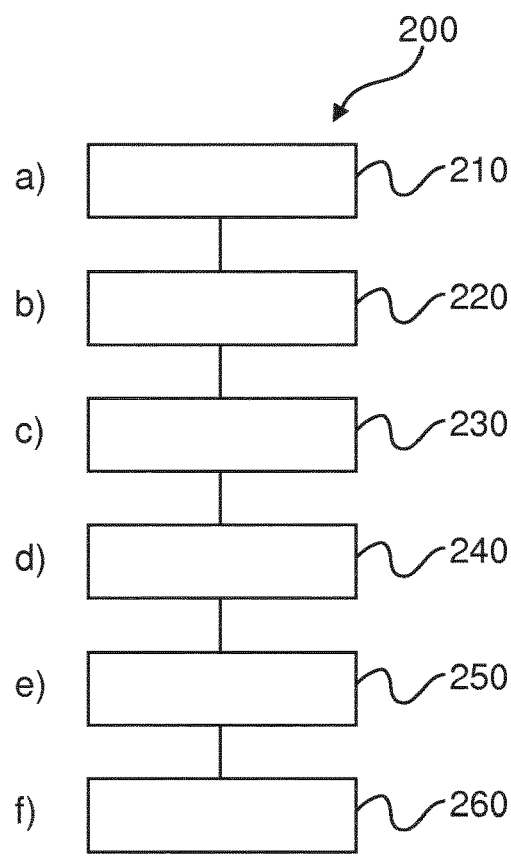
FIG. 3 shows a method for generating dual energy imaging data.

FIG. 3 shows a method 200 for generating dual energy X-ray imaging data in its basic steps. The method 200 comprises:

in a positioning step 210, also referred to as step a), positioning an X-ray detector relative to an X-ray source such that at least a part of a region between the X-ray source and the X-ray detector is an examination region for accommodating an object;

in a positioning step 220, also referred to as step b), positioning a grid filter between the examination region and the X-ray source;

in a producing step 230, also referred to as step c), producing by the X-ray source a focal spot on a target to produce X-rays;

in a moving step 240, also referred to as step d), moving by the X-ray source the focal spot in a first direction across a surface of the target; wherein, the grid filter has a structure in a first orientation such that the movement of the focal spot in the first direction results in an associated change in an intensity of X-rays transmitted by the grid filter;

in a moving step 250, also referred to as step e), moving by the X-ray source the focal spot in a second direction across the surface of the target that is orthogonal to the first direction; wherein, the grid filter has a structure in a second orientation orthogonal to the first orientation such that the movement of the focal spot in the second direction results in an associated change in an energy spectrum of X-rays transmitted by the grid filter;

in a detecting step 260, also referred to as step f), detecting with the X-ray detector at least some of the X-rays transmitted by the grid filter.

In an example, additional detectors can be placed behind the grid filter, in effect to measure a reference signal to check if the position in the first and second direction is correct, and that the attenuation and spectral filtration outside the object beam is consistent with that required for the object beam. In effect, this provides a performance check provided via an appropriate calibration.

In an example, the grid filter has a focal length associated with the structure in the first orientation, and wherein step b) comprises spacing the grid filter away from the focal spot of the X-ray source by a distance equal to the focal length.

In an example, the structure in the first orientation comprises a plurality of first lamellae spaced apart from one another, and wherein the first lamellae are made of a first material and wherein the grid filter between the first lamellae are made of the first material or a material relatively transparent to X-rays.

In an example, the plurality of first lamellae point towards a line on the target such that the focal spot when focused at a position on that line is associated with maximum X-ray transmission with respect to movement in the first direction.

In an example, the structure in the first orientation comprises a spatially varying absorbing profile with a minimum absorption associated with the center of the plurality of first lamellae and an increasing absorption profile associated with the structure in the first orientation extending either side of the center of the first lamellae.

In an example, the spatially varying absorption profile comprises a variation in the thickness of individual ones of the plurality of first lamellae.

In an example, the structure in the first orientation comprises a plurality of further lamellae spaced apart from one another and spaced laterally from the plurality first lamellae, and wherein the structure in the first orientation comprises a spatially varying absorbing profile with a minimum absorption associated with the center of the plurality of further lamellae. An increasing absorption profile is associated with the structure in the first orientation extending either side of the center of the further lamellae that is different to the increasing absorption profile associated with the structure in the first orientation extending either side of the center of the first lamellae.

In an example, the plurality of further lamellae point towards a line on the target such that the focal spot when focused at a position on that line is associated with maximum X-ray transmission with respect to movement in the first direction.

In an example, the grid filter has a focal length associated with the structure in the second orientation, and wherein the grid filter is spaced away from the focal spot of the X-ray source by a distance equal to the focal length.

In an example, the structure in the second orientation comprises a plurality of second lamellae spaced apart from one another, and wherein the second lamellae are made of a different material to the first lamella.

In an example, the plurality of second lamellae point towards the focal spot when at the position associated with maximum X-ray transmission.

Different elements of the apparatus, system and method for generating dual energy imaging data will now be described in more detail in conjunction with FIGS. 4-7.

Figure 4:
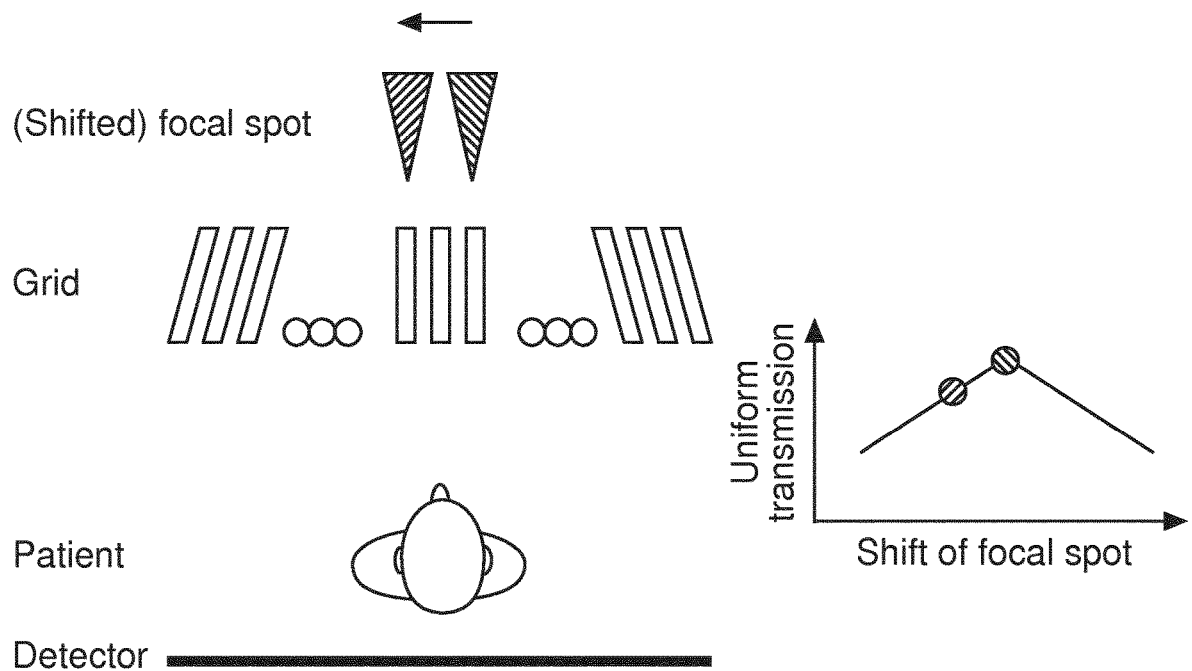
FIG. 4 shows a schematic example of a structure of a grid filter in a first orientation with movement of the position of X-ray emission in a first direction leading to a change in X-ray intensity.

FIG. 4 schematically shows a structure of a grid filter in a first orientation. This structure of the grid filter is placed close to the exit window of the X-ray source, between the X-ray source and the patient. The structure of the grid filter in this orientation has a 1-dimensional grating or grid like structure consisting of a series of lamellae that are angled towards focal spot of the x-ray source; where electrons are focused onto the target surface of the anode and from which X-rays are emitted. When the focal spot is in this aligned position there is a maximum in transmission through this 1-D structure of the grid filter. However, movement of the focal spot, through for example re-focusing at a laterally displaced position leads to the X-rays now angling through the lamellae and causing a drop in X-ray intensity because the grid filter in this orientation has a lower transmission. This is shown in FIG. 4. Thus the grid filter made up from a grating or focused grid-like structure close to an X-ray tube can be used to modulate the X-ray flux exiting this filter by using the X-deflection of the focal spot. Most current tubes have means to move the electron spot hitting the anode. This motion is often used to circumvent certain problems in the image reconstruction. By using a reconstruction algorithm which does not need this deflection, the deflection can be used to modulate the X-ray flux in a fast and dynamic way together with a grating or grid-like structure close to the tube. Thus a new way to be able to change the X-ray flux of the tube by placing the grid-like structure very close to the X-ray tube (so on the other side of the patient compared to normal anti-scatter grid use), and by using a focused grid with a focal distance equal to the distance to the X-ray focus it is assure that the transmission of X-rays through the grid yields a flat profile for all shifts of the focal spot in this direction. However only for one (nominal) position the transmission is maximal and shifting the focal spot away from this position in the direction perpendicular to the lamellae yields a lower overall transmission. In this was a homogeneous decrease in transmission is provided when the focal spot is moved away from the ideal position perpendicular to the lamellae direction to modulate the X-ray flux passing the grid by electronically steering the electron beam away from its ideal nominal position. In this manner, the X-ray flux (intensity) can be varied (modulated) in a very fast way without having any mechanically moving parts, and this can be utilized with most existing CT systems. It is also to be noted, that with just this 1-D structure a movement of the focal spot in the orthogonal direction does not lead to a change in transmission of the filter because the X-rays have the same angling through the lamellae.

To recall, in current systems, as the CT scanner rotates around the patient the cross-section of the patient is not constant, being somewhat elliptical. In the AP or PA projection the patient is usually thinner than in the side projection for abdominal imaging. In current CT systems the X-ray flux is controlled in such a way that the most challenging projection has sufficient SNR, so each projection is usable for the reconstruction, and for the AP and PA projection the SNR is better than the minimal requirement and a dose saving could be achieved if the X-ray flux in these projection was reduced. In current systems, because of the high rotation frequencies of the CT system, it is difficult to change the X-ray flux with the required speed and precision. Normally the X-ray flux is controlled by the electron beam current in the tube which depends on the temperature of the cathode and slightly on the acceleration voltage (depending on the exact design of the tube). The temperature of the cathode is controlled by a current which is superimposed on the high voltage at which most X-ray cathodes are. In current systems because of the high capacity of the voltage cables it is difficult to switch the cathode current in a fast way. In addition to that it takes some time for the cathode to heat up or cool down, so changing the electron beam current in this way is inherently slow. In recent times an electrostatic aperture (so-called fast tube grid switching GS) can be introduced in the tube which can quickly turn on or off the beam current. In this manner the average beam current can be controlled by pulse width modulation. This is however an expensive solution which requires additional cables and high voltage supplies. This solution is therefore restricted to the high-end CT X-ray tubes.

However, having a grid filter having the 1-D structure discussed above with respect to FIG. 4 expensive hardware modifications are not required, rather a very easy to make grid-like structure is used, which can be produced cheaply, together with the ability of many (CT) X-ray tubes to slightly move the X-ray focal spot w.r.t. the anode. This then enables the X-ray flux (X-ray intensity) through the patient to be modulated. Other X-ray tubes can be used that enable larger movement of the X-ray focal spot.

Continuing with the 1-D structure in this orientation of the grid filter as shown in FIG. 4, in between the interspacer material, lamellae made out of lead or tungsten or molybdenum are positioned in such a way that the lamellae all point towards one point or line in space. This combination produces a focused grid if this point is at a finite distance. The grid can have a cover plate to protect the delicate stack of lamellae against physical harm and/or moisture. A stacking process can be used to produce the grid, with each lamella positioned very accurately and then glued to the already existing stack. In such a way with modern production equipment, grids with various parameters, such as line pairs/cm, ratio or focal distance can be produced. By positioning of this 1D grating structure close to the X-ray tube, preferably inside or just below the collimator, a sharply reduced transmission when the focal spot is slightly moved can be effected. This is provided when the 1-D grating structure has sufficient ratio (=aspect ratio of the interspacer material in between the X-ray absorbing lamellae) enabling the X-ray flux entering the patient to be varied (modulated).

Figure 5:
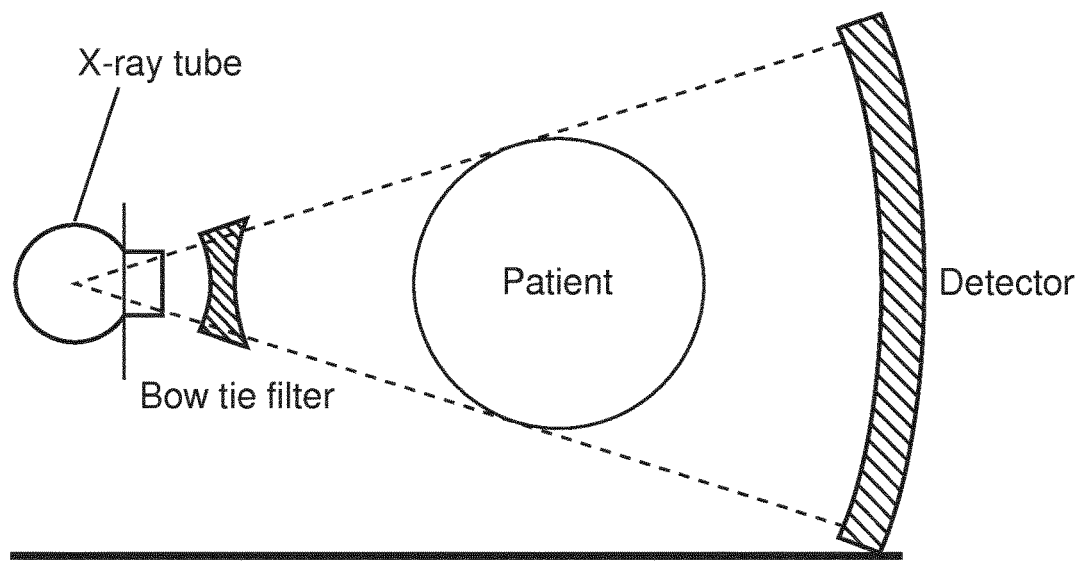
FIG. 5 shows a schematic example of a structure of a grid filter in a first orientation that acts as a Bow Tie filter.

FIG. 5 shows schematically further details relating to the 1-D structure of the grid filter discussed with respect to FIG. 4. The absorption profile of the 1-D structure actually has a Bow Tie profile. In this way in addition to being able to homogeneously change the intensity of the entire X-ray beam as discussed with respect to FIG. 4 through a movement of the focal spot, the center of the X-ray beam has a higher intensity than the edges to match the cross section of the human body. This is achieved by having the underlying structure between the lamellae having an appropriate absorption profile, being less absorbing in the center with increasing absorption to the sides and/or changing the lamellae thickness, with increasing thickness away from the center, and/or angling the lamellae slightly such that they do not all point towards the focal spot at the nominal maximum position, such that there is increased absorption towards the edges.

Thus, with reference to FIGS. 4-5, a 1-D structure of the grid filter provides a dynamic Bow Tie capability, with a Bow Tie absorption profile being able to be intensity modulated.

Figure 6:
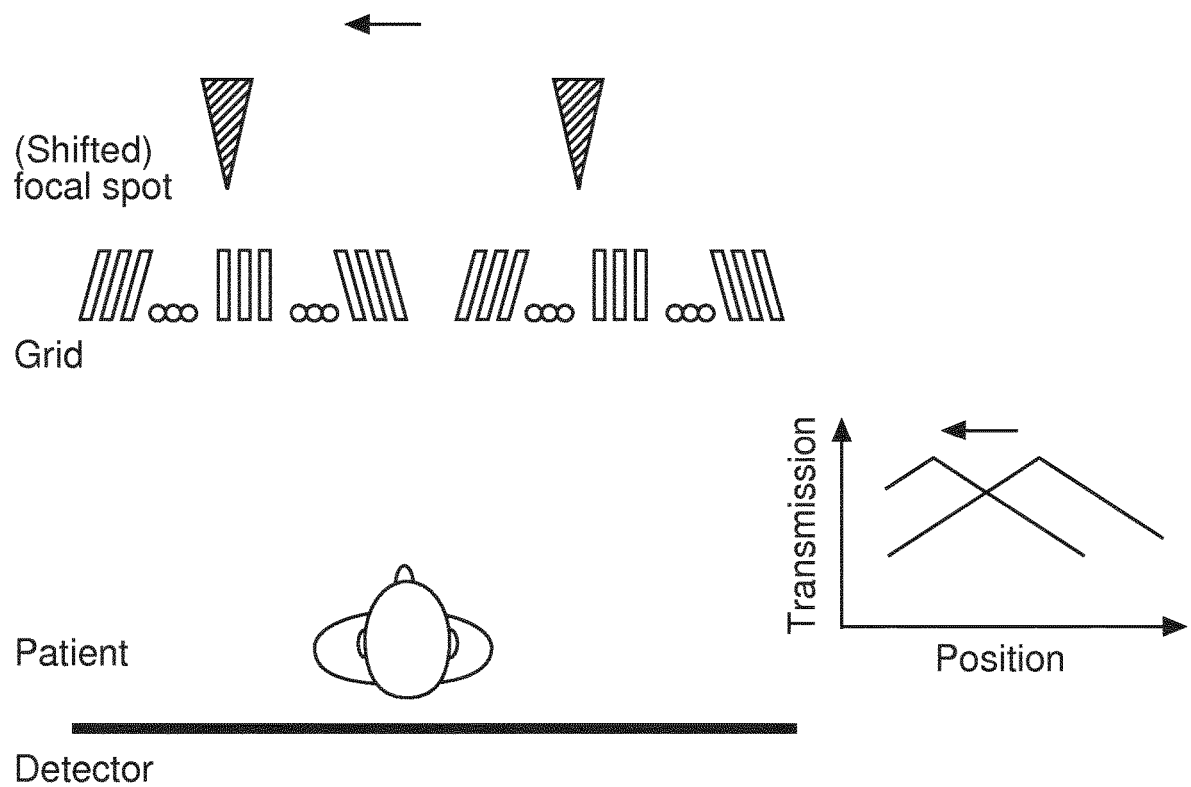
FIG. 6 shows a schematic example of a structure of a grid filter in a first orientation with movement of the position of X-ray emission in a first direction leading to a change from one Bow Tie filter to another Bow Tie filter.

Furthermore, patients come in different sizes, for example small children have a smaller chest than that of large men. Therefore, as shown in FIG. 6, the structure of the grid filter in this orientation does not have just one 1-D dynamic Bow Tie structure, but has more than one stacked to the side of each other. A small movement of the focal spot enables intensity modulation for a specific Bow Tie, for example that optimized for adults, Then, when examining a small child, a larger movement of the focal spot can be used to utilize a different Bow Tie optimized for children. For that Bow Tie small movements of the focal spot can be used to modulate the intensity for that Bow Tie for children in the same manner as described above.

Figure 7:
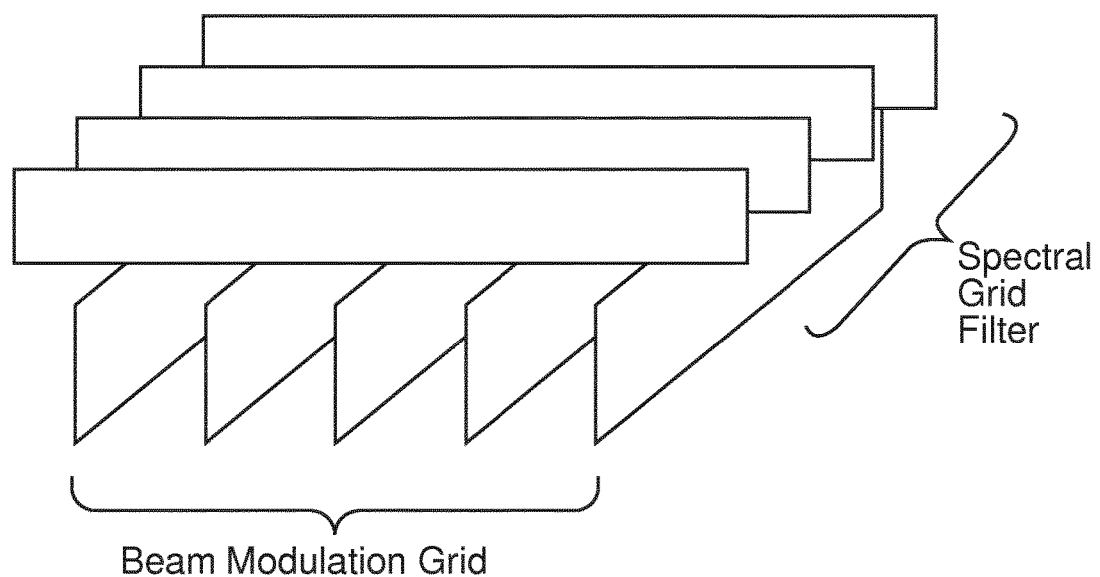
FIG. 7 shows an example of a grid filter having a 1-D beam intensity modulating structure and an orthogonally orientated 1-D beam spectral energy modulating structure.

However, further diagnostic information can be provided from an X-ray examination, if dual energy data sets are provided. Therefore, as shown in FIG. 7, the grid filter has a second 1-D structure that is orthogonal to the first 1-D structure. The first 1-D structure can for simplicity be termed a beam modulation grid, and the second 1-D structure can be termed a spectral grid filter. The spectral grid filter is similar to the beam modulation grid, being made from lamellae but these are of a different material to the first lamellae. Thus, as discussed above as the focal spot is moved in the first direction there is a homogenous change in beam intensity, where this X-ray beam has a first energy spectrum. However, the focal spot can be moved in a direction perpendicular to the lamellae of the spectral grid filter, which leads to a change in the energy spectrum. In this way, as the gantry rotates around the patient, the intensity can be gradually modulated at possibly a low frequency to match the patients rotationally non-symmetric profile. But from one acquisition frame to the next, the focal spot can be moved in this second direction from a first position to a second position and back to the first repetitively. In this manner, at each viewing angle, albeit with a very slight rotational movement between acquisitions, dual energy data has been acquired from which the resultant images can be de-convolved into material basis sets. Thus, intensity modulation can be at the Hz, tens of Hz or hundreds of Hz frequency, whilst the spectral modulation can be at the 5 kHz, 10 kHz frequency or so. There can also be the situation when no filtration is used for one frame, and then 2, 3, 4 or 5 subsequent frames are acquired at higher filtration.

Thus, the grid filter has a first Grid optimized for the dynamic bowtie functionality and aligned with the slow changing focal spot position controlled in one direction. The grid filter also has a second Grid that is on top (or bottom) of the first grid, that is rotated and mainly designed as a spectral filter. The movement of the focal spot in the orthogonal direction then controls the pathway through the filter lamella or the direct unfiltered path to provide two different X-ray beam energy spectrums. Because of the rotated and aligned stacking of both elements an independent control of the intensity modulation (slow) on the fast spectral modulation is possible.

As discussed above, the lamella structures for both grids can be produced in foil stacking technologies. Then, for interfacing both grids to a stacked grid the extension of some lamella (every x-th lamella) would be the mechanical intersection to the other grid fitting into a diced slot that is then glued together or welded. Additive production technologies also enable complicated structures like fixing elements of 2 grids in the frame or just the simple frame around the 2 individual layers with mechanical fine-positioning elements before gluing together or fixing in a defined position. An individual 3D printed frame with x-ray absorbing materials like lead or tungsten or Molybdenum via laser sintering is a technology that can be used to build the frame for the foil stacked lamellas.

In another exemplary embodiment, a computer program or computer program element is provided that is characterized by being configured to execute the method steps of the method according to one of the preceding embodiments, on an appropriate system.

The computer program element might therefore be stored on a computer unit, which might also be part of an embodiment. This computing unit may be configured to perform or induce performing of the steps of the method described above. Moreover, it may be configured to operate the components of the above described apparatus and/or system. The computing unit can be configured to operate automatically and/or to execute the orders of a user. A computer program may be loaded into a working memory of a data processor. The data processor may thus be equipped to carry out the method according to one of the preceding embodiments.

This exemplary embodiment of the invention covers both, a computer program that right from the beginning uses the invention and computer program that by means of an update turns an existing program into a program that uses invention.

Further on, the computer program element might be able to provide all necessary steps to fulfill the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. An apparatus for generating dual energy X-ray imaging data, comprising:
    an X-ray source;
    a grid filter;
    an X-ray detector;
    wherein the X-ray source is configured to produce a focal spot on a target to produce X-rays;
    wherein the X-ray source is configured to move the focal spot in a first direction across a surface of the target;
    wherein the X-ray source is configured to move the focal spot in a second direction across the surface of the target that is orthogonal to the first direction;
    wherein the X-ray detector is positioned relative to the X-ray source such that at least a part of a region between the X-ray source and the X-ray detector is an examination region for accommodating an object;
    wherein the grid filter is positioned between the examination region and the X-ray source;
    wherein the grid filter has a structure in a first orientation such that a movement of the focal spot in the first direction is configured to result in an associated change in an intensity of X-rays transmitted by the grid filter;
    wherein the grid filter has a structure in a second orientation orthogonal to the first orientation such that a movement of the focal spot in the second direction is configured to result in an associated change in an energy spectrum of X-rays transmitted by the grid filter; and
    wherein the X-ray detector is configured to detect at least some of the X-rays transmitted by the grid filter.

2. Apparatus according to claim 1, wherein the grid filter has a focal length associated with the structure in the first orientation, and wherein the grid filter is spaced away from the focal spot of the X-ray source by a distance equal to the focal length.

3. Apparatus according to claim 1, wherein the structure in the first orientation comprises a plurality of first lamellae spaced apart from one another, and wherein the first lamellae are made of a first material and wherein the grid filter between the first lamellae is made of the first material or a material transparent to X-rays.

4. Apparatus according to claim 3, wherein the plurality of first lamellae point towards a line on the target such that the focal spot when focused at a position on that line is associated with maximum X-ray transmission with respect to movement in the first direction.

5. Apparatus according to claim 3, wherein the structure in the first orientation comprises a spatially varying absorbing profile with a minimum absorption associated with the center of the plurality of first lamellae and an increasing absorption profile associated with the structure in the first orientation extending either side of the center of the first lamellae.

6. Apparatus according to claim 5, wherein the spatially varying absorption profile comprises a variation in the thickness of individual ones of the plurality of first lamellae.

7. Apparatus according to claim 5, wherein the structure in the first orientation comprises a plurality of further lamellae spaced apart from one another and spaced laterally from the plurality first lamellae, and wherein the structure in the first orientation comprises a spatially varying absorbing profile with a minimum absorption associated with the center of the plurality of further lamellae and an increasing absorption profile associated with the structure in the first orientation extending either side of the center of the further lamellae that is different to the increasing absorption profile associated with the structure in the first orientation extending either side of the center of the first lamellae.

8. Apparatus according to claim 7, wherein the plurality of further lamellae point towards a line on the target such that the focal spot when focused at a position on that line is associated with maximum X-ray transmission with respect to movement in the first direction.

9. Apparatus according to claim 1, wherein the grid filter has a focal length associated with the structure in the second orientation, and wherein the grid filter is spaced away from the focal spot of the X-ray source by a distance equal to the focal length.

10. Apparatus according to claim 1, wherein the structure in the second orientation comprises a plurality of second lamellae spaced apart from one another, and wherein the second lamellae are made of a different material to the first lamella.

11. Apparatus according to claim 10, wherein the plurality of second lamellae point towards the focal spot when at the position associated with maximum X-ray transmission.

12. A system for X-ray imaging an object, comprising:
an apparatus for generating dual energy X-ray imaging data according to claim 1;
a processing unit; and
an output unit;
wherein the processing unit is configured to control the apparatus, and is configured to control the output unit;
wherein the X-ray detector is configured to provide the processing unit with data relating to the detection of X-rays;
wherein the output unit is configured to output data representative of the object.

13. A method for generating dual energy X-ray imaging data, comprising:
positioning an X-ray detector relative to an X-ray source such that at least a part of a region between the X-ray source and the X-ray detector is an examination region for accommodating an object;
positioning a grid filter between the examination region and the X-ray source;
producing by the X-ray source a focal spot on a target to produce X-rays;
moving by the X-ray source the focal spot in a first direction across a surface of the target; wherein the grid filter has a structure in a first orientation such that the movement of the focal spot in the first direction results in an associated change in an intensity of X-rays transmitted by the grid filter;
moving by the X-ray source the focal spot in a second direction across the surface of the target that is orthogonal to the first direction; wherein; the grid filter has a structure in a second orientation orthogonal to the first orientation such that the movement of the focal spot in the second direction results in an associated change in an energy spectrum of X-rays transmitted by the grid filter;
detecting with the X-ray detector at least some of the X-rays transmitted by the grid filter.

\* \* \* \* \*